Figure 1:
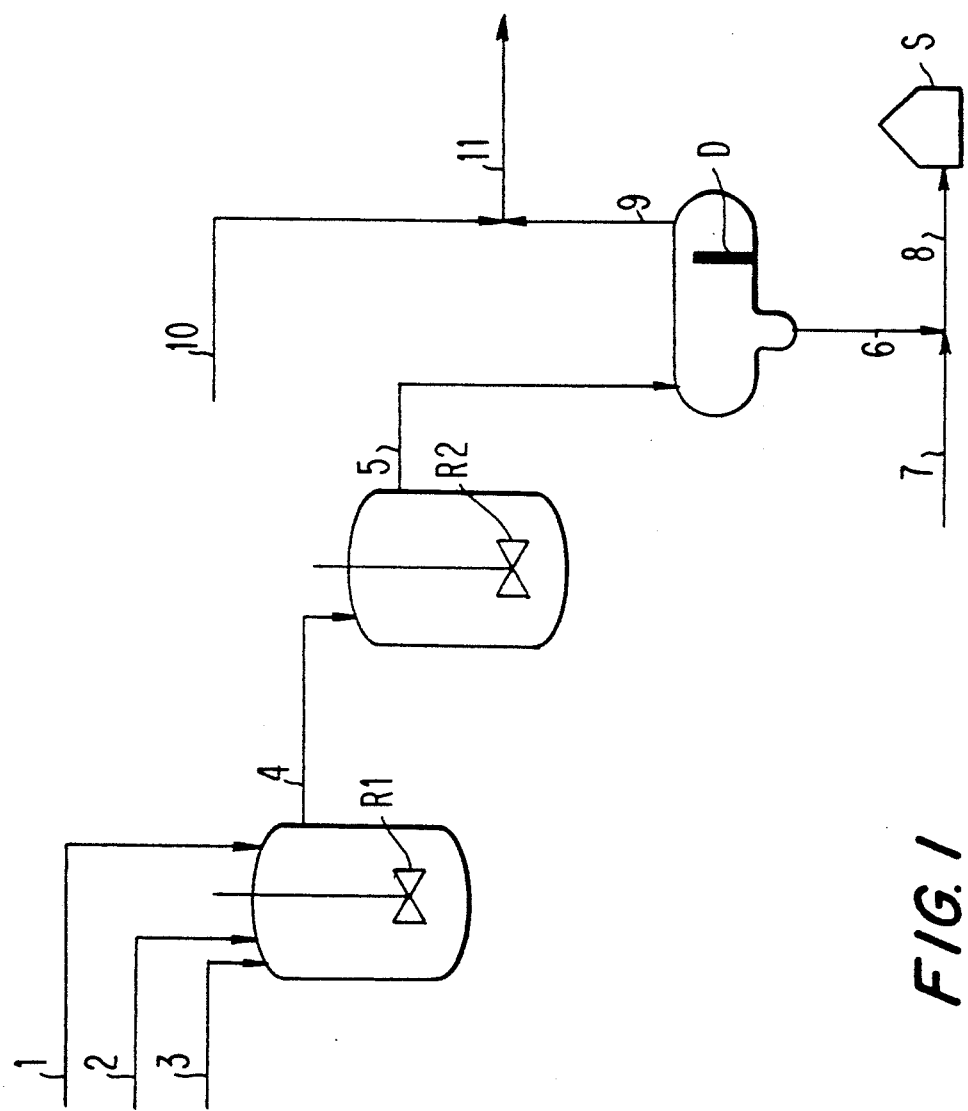

United States Patent [19]

Cavallotti et al.

[11] Patent Number: 5,208,340
[45] Date of Patent: May 4, 1993

[54] PROCESS FOR PRODUCING AN ARYL-IMIDO-PERALKANOIC ACID BY OXIDIZING THE CORRESPONDING ARYL-IMIDO-ALKANOIC ACID WITH HYDROGEN PEROXIDE

[75] Inventors: Claudio Cavallotti, Milan; Michele Merenda, Frugarolo; Alessandro Zaro, Alessandria; Attilio Lagostina, Spinetta Marengo; Ugo P. Bianchi, Verona, all of Italy

[73] Assignee: Ausimont S.p.A., Milan, Italy

[21] Appl. No.: 805,480

[22] Filed: Dec. 11, 1991

[30] Foreign Application Priority Data

Dec. 13, 1990 [IT] Italy .................. 22374 A/90

[51] Int. Cl.$^5$ .............. C07D 209/48; C07D 209/66; C11D 3/395; D06L 3/02
[52] U.S. Cl. ...................................... 546/98; 548/479
[58] Field of Search ............................ 548/479; 546/98

[56] References Cited

U.S. PATENT DOCUMENTS 4,172,086 10/1979 Berkowitz ........................... 562/2

FOREIGN PATENT DOCUMENTS 0000970 3/1979 European Pat. Off. ............ 562/6
325288 7/1989 European Pat. Off. ............ 548/479

Primary Examiner—Floyd D. Higel
Attorney, Agent, or Firm—Bryan Cave

[57] ABSTRACT

Process for producing an aryl-imido-peralkanoic acid by means of the peroxidation with $H_2O_2$ of the corresponding alkanoic (non-peroxy) acid, in the presence of a strong acid with a pKa value equal to, or lower than 3, and in the presence of a halogenated solvent, characterized in that said solvent is $CH_2Cl_2$ or $CHCl_3$, that the amount of alkanoic acid submitted to peroxidation is equal to or smaller than the solubility threshold of said alkanoic acid (in said solvent) and that a solution of said acid in said solvent is reacted with $H_2O_2$ (at 10°–35° C.), with the molar ratio of said strong acid to said alkanoic acid being lower than 2.

19 Claims, 3 Drawing Sheets

PROCESS FOR PRODUCING AN ARYL-IMIDO-PERALKANOIC ACID BY OXIDIZING THE CORRESPONDING ARYL-IMIDO-ALKANOIC ACID WITH HYDROGEN PEROXIDE

The present invention relates to a process for producing, in a continuous mode, an arylimidoperalkanoic acid, in particular ε-phthalimidoperhexanoic acid. ε-phthalimidoperhexanoic acid—designated in the following as "phthalimidoperhexanoic acid" or, more briefly, "PAP"—is used as a bleaching agent in low-temperature washing of textile products, as reported in European patent 325288 and it is also used as a sanitizer, an oxidizer agent and a free-radical generator, in the processing and treatment of textile products, paper and wastes, and is useful in chemical syntheses involving the formation of intermediates and polymers.

From U.S. Pat. No. 4,172,086, the contents of which are an integral part of the instant specification, producing peralkanoic acids (in particular peralkanedioic acids) by oxidizing the corresponding alkanoic (non-peroxy) acids with hydrogen peroxide and in the presence of large amounts of $H_2SO_4$ or oleum, by feeding to the reaction zone the acid to be peroxidized, as a suspension (in halogenated organic solvents), is known; unfortunately, the amounts of $H_2SO_4$ were rather large (preferably of from 2 to 3 mol per mol of alkanoic acid) and the necessary temperatures for peroxidizing the high-molecular-acids ($C_{10}+$) were also rather high (40°–60° C.).

Furthermore, when the present inventors tried to use a suspension of a phthalimidoalkanoic acid in some of the halogenated solvents mentioned by said patent (carbon tetrachloride, monochlorobenzene, and so forth) in a continuous process, the test had to be discontinued after a few minutes due to the clogging of the equipment, caused by an enormous increase in reaction mixture viscosity (see Comparative Example No. 4).

The present inventors have now developed a novel process which makes it possible to peroxidize arylimidoalkanoic acids in a continuous mode at low temperatures and on a large scale. The present process is safe, flexible, and requires relatively low amounts of reactants, additives and auxiliary services.

In its widest aspect, the present invention relates to a process for producing in a continuous mode an arylimidoperalkanoic acid having formula (I):

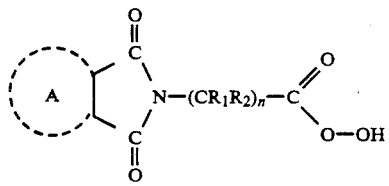

in which n is an integer comprised within the range of from 3 to 7 and:
A is a benzene or naphthalene ring, optionally bearing one or more substituent groups, in particular bearing a carboxy group;
$R_1$ and $R_2$, which can be either equal to, or different from, each other, are selected from among H and the linear or branched, possibly substituted, alkyl groups of from 1 to 5 carbon atoms;

by means of the peroxidation with $H_2O_2$ of the corresponding arylimidoalkanoic (non-peroxy) acid of formula II:

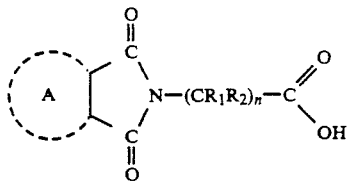

in the presence of a strong acid with a pKa value equal to, or lower than, 3 and preferably equal to, or lower than, 1, and in the presence of a halogenated organic solvent, characterized in that:
(A) said halogenated solvent is selected from among methylene chloride ($CH_2Cl_2$) and trichloromethane ($CHCl_3$);
(B) a solution is prepared of the arylimidoalkanoic acid to be peroxidized (i.e., the raw material) in said halogenated solvent, by taking care that the amount of raw material dissolved is:
  (i) either equal to, or smaller than, the solubility threshold of said raw material in said solvent at the reaction temperature as defined hereinunder in (C);
  (ii) higher than that amount of raw material which stoichiometrically corresponds to the solubility threshold of said peralkanoic acid in said solvent [at the same temperature as defined above];
(C) the solution obtained according to (B) is continuously reacted, at 10°–35° C., with aqueous $H_2O_2$, in the presence of said strong acid, with the molar feed ratio of said strong acid to the acid to be peroxidized being adjusted at a value smaller than 2 (preferably smaller than 1.3), with a reaction product constituted by two liquid phases (an aqueous phase and an organic phase) being thereby obtained;
(D) said reaction product is separated into two component single homogeneous phases, said peralkanoic acid and halogenated solvent are recovered from the organic phase and said halogenated solvent is recycled to the dissolving step as described in (B).

In particular, $R_1$ and $R_2$ are selected from among H and $C_1$–$C_5$ alkyl groups bearing carboxy, percarboxy, hydroxy (OH), nitro ($NO_2$) or $C_1$–$C_5$ alkoxy substituents. Examples of peracids which can be obtained according to the invention are phthalimidoperalkanoic acids of formula (III) and 1,8-naphthaleneimidoperalkanoic acids of formula (IV) (a particularly interesting acid is ε-phthalimidoperhexanoic acid):

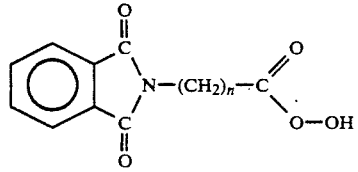

-continued

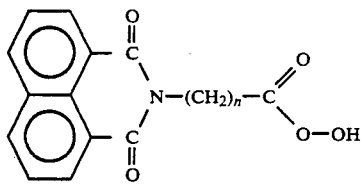

(IV)

The selection of the solvent and of the concentration values is critical; the present inventors tried to use very similar solvents from the chemical point of view, such as carbon tetrachloride, monochlorobenzene or acetonitrile, always meeting with serious drawbacks, which are discussed in greater detail below.

Going into detail, the present inventors unexpectedly observed, contrary to the teaching of the prior art, that not only is the particular peroxy product (PAP), soluble but also that the particular raw material (PAC) is even more soluble, in the particular halogenated solvents used in the present thus allowing the reaction to proceed according to a different mechanism from that which is disclosed in U.S. Pat. No. 4,172,086. The novel mechanism results in high conversion and yield under low temperature, low viscosity and internal system temperature control conditions. In addition, a very efficient product recovery can be obtained from the inorganic phase. Of course, the pressure should be such as to keep the system in the liquid phase. Table 1 shows some solubility data experimentally observed by the present inventors.

TABLE 1 (*)

| Solvent | Solubility (g per 100 cm$^3$ of solvent) | |
|---|---|---|
| | PAC | PAP |
| Dichloromethane | | |
| at 14° C.: | 51.1 | 26.3 |
| at 25° C.: | 67.3 | 35.2 (**) |
| Trichloromethane | | |
| at 14° C.: | 52.3 | 26.1 |
| at 25° C.: | 67.9 | 34.9 |

Figure 3:
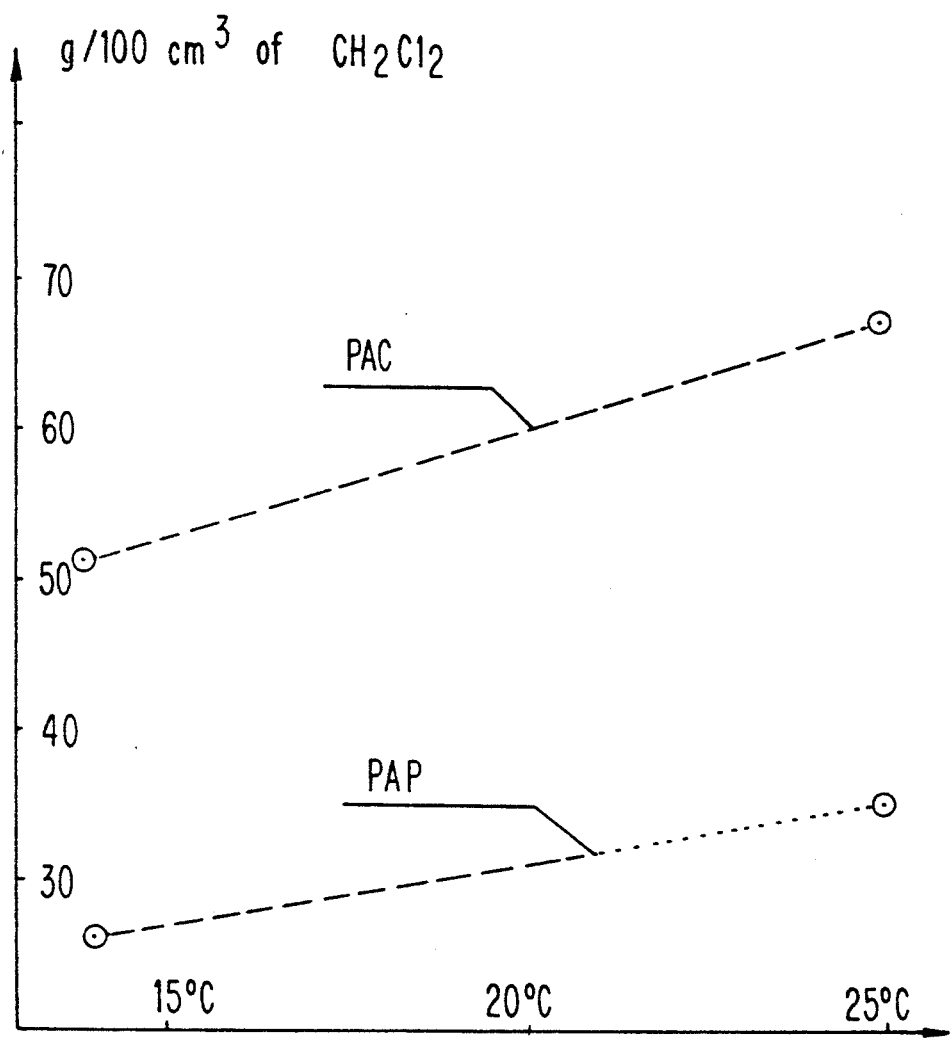

(*) See also chart of FIG. 3.
(**) Estimated value

The new process makes it possible to carry out the peroxidation reaction in a mode under controlled and safe conditions, with very low temperatures and very low aliquots of strong acid and hydrogen peroxide, by preferably using CSTR (Continuous Stirred Tank Reactor) mixing reactors of varying sizes which can be used on a commercial level. As an alternative, an external-recycle reactor or a static mixer might be used; furthermore, the feed of the reactants may be gradual, i.e., it can be accomplished at a plurality of successive feed points. These reactors and these operating methods are disclosed, e.g., in European patent 0970, the contents of which constitute an integral part of the present specification. Cheapness, flexibility and the ability to obtain considerable scale increases while maintaining safety are important advantages of the process according to the invention.

According to a particularly advantageous form of a practical embodiment of the invention, the adoption of the following, either complementary or alternative, operating instructions, is recommended for peroxidizing PAC:

continuous feed of a solution containing at least 20% (preferably 25–30%) by weight of acid to be peroxidized (in particular, PAC in a halogenated solvent);

continuous feed of aqueous hydrogen peroxide at 50–90% by weight (preferably 60–80%) and with a molar ratio of $H_2O_2$ (100%) to PAC of from 1 to 2 (preferably of from 1.01 to 1.6);

molar ratio of the strong acid to PAC comprised within the range of from 0.50 to 1.29; while said strong acid can be selected, e.g., from among sulfuric acid, oleum, methanesulfonic acid, trifluoromethanesulfonic acid, fluorosulfonic acid and their mixtures; and so forth. The amount of strong acid can be considerably reduced if, before (or during) the contact with the strong acid, a so-called "solid acid" is used; with said solid acid being selected from the group consisting of the cation exchange resins, of strong type, and the zeolite aluminosilicates, of PENTASIL type (in their acidic form; e.g., HZSM5 and HZSM11). The contact with a bed of said resins or said aluminosilicates can reduce the value of the ratio of the strong acid to PAC to be peroxidized, even down to very low levels (0.50, by mol).

At the end of the peroxidation, in one or more reactors (in parallel, or, preferably, in cascade), the double-phase reaction mixture must be separated (phase separation), e.g., in a separation tank. The acidic/aqueous phase can be subsequently diluted with deionized water, in order to facilitate the recovery of the residual product (PAP) from said acidic/aqueous phase, and reduce the riskful instability thereof. The amount of dilution water is generally comprised within the range of from 0.5 to 1.5 liters per each liter of separated aqueous phase. As an alternative, the dilution can be performed before carrying out the phase separation. The organic phase, containing traces of residual acidity, is usually neutralized with a slightly alkaline solution, containing, e.g.: $NaHCO_3$, $Mg(HCO_3)_2$, NaOH, and so forth; as an alternative, said organic phase can be caused to flow through a bed of anion exchange resins, or of solid alkali-metal compounds or alkali-earth metal compounds ($NaHCO_3$, $Na_2CO_3$, $MgCO_3$, and so forth).

In the following, description a particular practical embodiment of the process according to the invention is disclosed with the aid of FIG. 1. Of course, both the description and the figure are supplied for merely illustrative purposes, and in no way should they be construed as being limitative of the scope of the invention.

Viewing FIG. 1, a concentrated solution of ε-phthalimidohexanoic acid (PAC) in a halogenated solvent (1), aqueous hydrogen peroxide (2) and the strong acid (3), e.g., $H_2SO_4$, are fed to reactor "R1", kept at room temperature. In that way, a system is obtained, which consists of two liquid phases. Such phases constitute the reactant system, characterized by low viscosity values and ease of fluid-dynamic dispersion. The normal stirring systems can thus secure exchange surface areas per volume unit, which are large enough so as not to confine the specific production capacity of the reactant system within a limiting kinetic control by the phase transfer. Furthermore, such a system is characterized by a high capability of self-control of possible local heat accumulations, deriving from the instability and degradation of reactants and products (the mass is dispersed throughout the reactor as a continuous fluid, without stagnation pockets due to viscosity gradients, and without any local accumulations of solid phase, and is thermally buffered by an excess of low-boiling solvent). Said system is furthermore characterized by an easy processability, in that its phases can be easily separated, by simple decantation (under rest conditions).

The reactant mixture (4) enters a second reactor R2 similar to the first reactor "R1". Inside reactor "R2" peroxidation is completed. The ultimate effluent (5) is submitted to phase-separation inside the separation tank "D". The acidic/aqueous phase (6) is then moderately diluted with deionized water (7), for safety reasons, and in order to enable that aliquot of product (PAP) which is not dissolved in the organic phase to be effectively recovered by back-extraction with the reaction solvent. The diluted solution (8) can be stored in the tank "S", or it can be directly sent to the back-extraction. The organic phase (9), in which traces of residual acidity exist, is neutralized with a weakly alkaline solution (10); as an alternative, the organic phase can be neutralized, as already said, by being caused to flow through a solid neutralizing bed. From the organic PAP solution (11), the product can be easily separated with the required purity level, e.g., by crystallization of the solute (by taking advantage of the considerable temperature dependence of its solubility in the solvent), and therefore it can be recovered by filtration (and/or centrifugation) and drying. According to an alternative route, as said in the following, the product (PAP) can be recovered by distilling off the solvent.

Figure 2:
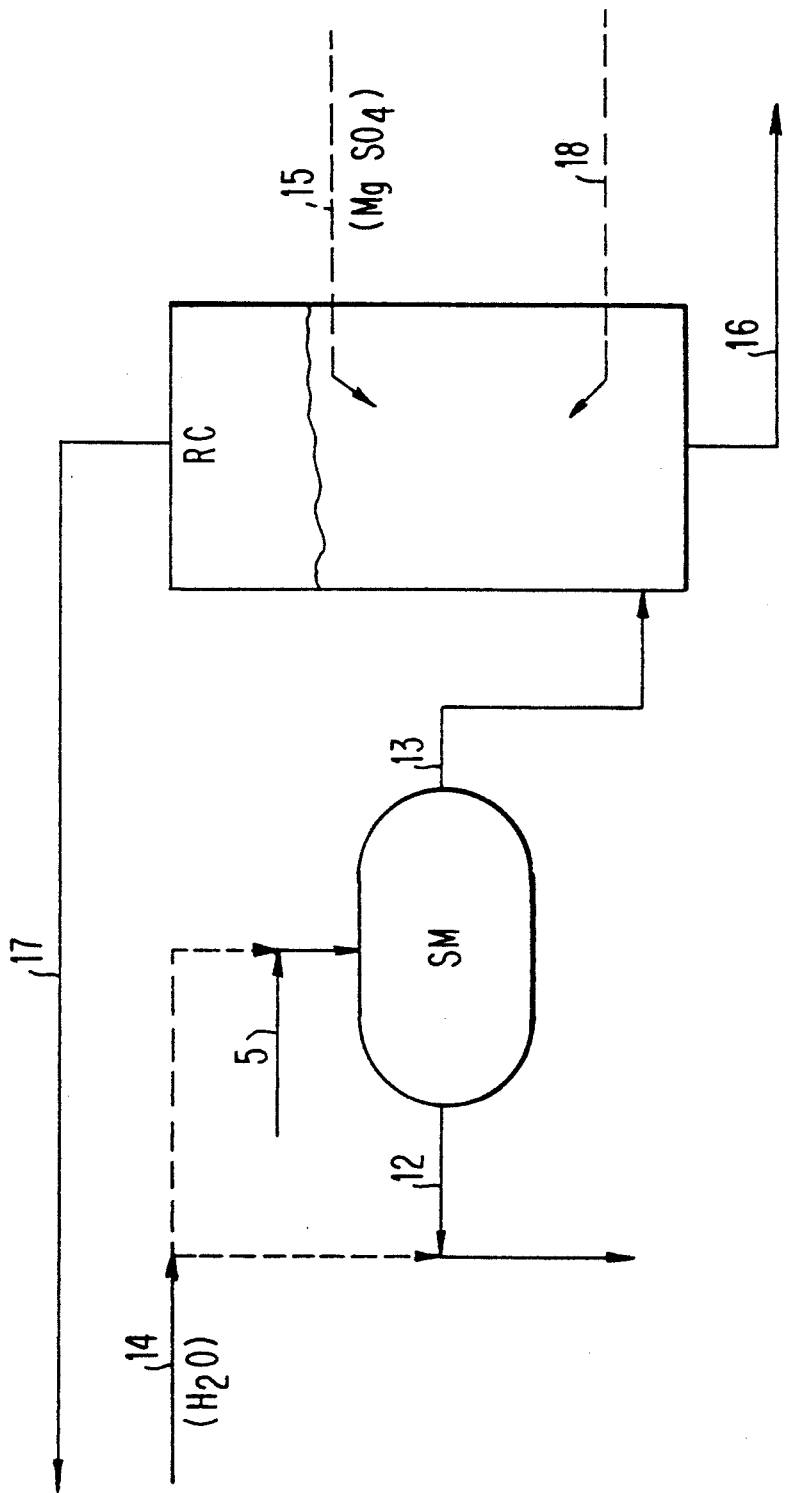

Another form of practical embodiment of the process according to the present invention is depicted in FIG. 2.

Viewing said FIG. 2, the reaction effluent (5) is phase-separated in an "SM" equipment piece, from which an aqueous phase (12) and an organic phase (13) outflow; a deionized water stream (14) is added, for such purposes as cited hereinabove, to the feed stream (5), and/or to the aqueous phase (12). The organic phase (13) is sent to a recovery section "RC", in which it is preferably admixed with the salt of an alkali-earth metal (15), e.g., magnesium sulfate ($MgSO_4$), and in which the following are recovered:

(a) the peracid (16), as solid particles, or as a concentrated slurry;
(b) the solvent (17), which is recycled to the reaction zone (peroxidation). The recovery of the solvent can take place in several ways. For example, one might drastically cool the mixture and then carry out a filtration (and/or a centrifugation), or the solvent can be removed by distillation. Said distillation can be performed in vacuum, or it can be a steam distillation, and so forth; see, e.g., the steam stream (18) shown in the figure.

The solvent, whichever way it is recovered can be fully recycled.

The following examples are supplied for merely illustrative purposes, and in no way should they be constructed as being limitative of the scope of the invention.

In all continuous-run examples, the following equipment was used:
vertical glass reactors, each having a capacity of 1.8 liters of with variable discharge level, equipped with jacket, flanged head, propeller stirrer (with 6 blades revolving at 650 rpm) and baffles (4 elements);
a horizontal separation tank (phase separation unit) made from glass, having a capacity of 0.7 liters of capacity, provided with a storage well and a partition wall.

EXAMPLE 1

0.42 kg/hour of $H_2SO_4$ (at 96% by weight), 0.23 kg/hour of $H_2O_2$ (at 70% by weight) and 4.17 kg/hour of a PAC solution (at 20% by weight) in methylene chloride were simultaneously and continuously charged to the facility depicted in FIG. 1. The reaction temperature was kept at 25° C. by cooling with cold water flowing through the reactor jacket. In that way, after phase separation, two liquid phases, i.e., a heavy, acidic phase (0.68 kg/hour) and a light organic phase (4.14 kg/hour) were obtained inside the "D" tank. The organic phase was continuously neutralized with an aqueous solution of $NaHCO_3$ and $Na_2SO_4$. After phase separation and crystallization, 0.79 kg/hour was obtained of $\epsilon$-phthalimidoperhexanoic acid (PAP) with iodometric titer higher than 99%, and a yield, relatively to the reactant (PAC), of 88%.

EXAMPLE 2

7.09 kg/hour of a PAC solution (at 23.5%) in $CHCl_3$, 0.83 kg/hour of $H_2SO_4$ (at 96%) and 0.47 kg/hour of $H_2O_2$ (at 70%) were fed to the same facility as of Example 1. The reaction temperature was kept at 25° C. by cooling with cold water flowing through the reactor jacket. After phase separation, the residual mineral acidity was removed by filtering the product solution (in $CHCl_3$) on a bed of solid $MgCO_3$. The product was then separated from the solvent by crystallization, by cooling, and, after filtration and drying, 1.57 kg/hour was obtained of PAP with iodometric titer higher than 99%. The overall yield, relatively to PAC (excluding recycles), was 89%.

EXAMPLE 3

Comparative Example; Batchwise Test with $CCl_4$ 300 g of $CCl_4$, 70.4 g of PAC and 35 g of $H_2SO_4$ (at 96%) were charged to a calorimetric reactor of 500 $cm^3$ of capacity, equipped with mobile-blade stirrer and thermometer, dipped in a circulating water bath at 25° C. The mixture was heterogeneous, with undissolved PAC in suspension; said mixture was stirred at 25° C. and 19.5 g of $H_2O_2$ (at 70%) was added to it. After 30 minutes, with stirring being continued, still at 25° C., the reaction mixture, which was heterogeneous and pastelike, with a large amount of suspended product, was discharged into 500 $cm^3$ of cold, deionized water (5° C.) and filtered, with great difficulty, through a porous frit filter and under vacuum. The isolated product was subsequently slurried in 100 $cm^3$ of deionized water and was neutralized, to pH 6, with strong stirring, with an aqueous solution of $Na_2CO_3$ (at 10%). The neutralized product was filtered once more and was dried at 25° C. for 48 hours (under vacuum) in a $CaCl_2$ containing drier. In that way, 62 g was obtained of a waxy product containing 62% of PAP (by iodometric assay) and with a yield of 51.7% (relatively to PAP).

EXAMPLE 4

Comparative Example: Continuous Test with $CCl_3$

The test of Example 3 was repeated, but operating continuously in a facility of the same type as described in Example 1 and FIG. 1. The result, which was clearly negative, reported in Table 2, shows once more that only a very limited number of halogenated compounds ($CH_2Cl_2$ and $CHCl_3$) can lead to satisfactory results, while even slightly different compounds, such as CCl₄, are decidedly excluded from commercial use.

EXAMPLE 5

Comparative Example: Continuous Test with a PAC Excess "Suspended" in CH₂Cl₂

The test of Example 1 was repeated by continuously feeding 2.08 kg/hour of a slurry containing a PAC amount much larger than the reactant solubility threshold (approximately 89 g per each 100 cm³ of methylene chloride). The temperature was kept at 25° C. by cooling with water flowing through the reactor jacket; as in Example 4, the test had to be discontinued after about 10 minutes, due to equipment clogging.

EXAMPLE 6

Comparative Example: Test at a Too High Temperature

The test of Example 2 was repeated, with the reaction temperature being increased up to 60°–65° C., by means of a controlled heating with hot water flowing through the reactor jacket. 1.40 kg/hour of PAP was obtained, with a iodometric titre of 90.4%; the yield, relatively to PAC (excluding the recycles) was of only 71.6%.

EXAMPLE 7

Example 1 was repeated at a temperature of 30° C. by lowering the H₂SO₄ (100%)/PAC molar ratio to the value of 1.200. A 86% yield was obtained, as reported on Table 2.

EXAMPLE 8

Example 7 was repeated by still lowering the H₂SO₄ (100%)/PAC molar ratio to the value of 1.000.

A 79% yield was thus obtained, as reported on Table 2.

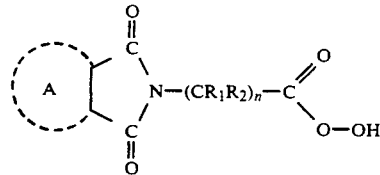

wherein A is selected from the group consisting of benzene, 1,2-naphthalene or 2,3-napthalene rings, or

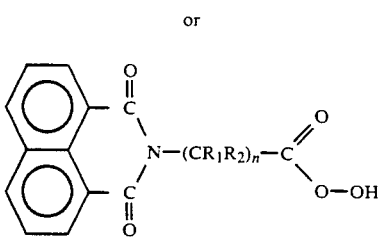

TABLE 2

| Example | Process Type | Ratio of H₂SO₄ (100%) to PAC (by mol) | Ratio of H₂O₂ (100%) to PAC (by mol) | Halogenated Organic Solvent | Ratio of PAC to Solvent (by weight) | T (°C.) | Residence Time | Yield |
|---|---|---|---|---|---|---|---|---|
| 1 | Continuous | 1.288 | 1.48 | CH₂Cl₂ | 20:80 | about 25 | 30 min | 88 |
| 2 | Continuous | 1.274 | 1.52 | CHCl₃ | 23.5:76.5 | about 25 | 30 min | 89 |
| 3[1] | Batchwise | 1.270 | 1.49 | CCl₄ | 19:81 | about 25 | 30 min | 51.7 |
| 4[1] | Continuous | 1.270 | 1.49 | CCl₄ | 19:81 | about 25 | — | 2 |
| 5[1] | Continuous | 1.288 | 1.48 | CH₂Cl₂ | 89 g of PAC per 100 cc of solvent | about 25 | — | 2 |
| 6[1] | Continuous | 1.274 | 1.52 | CHCl₃ | 23.5:76.5 | 60–65 | 30 min | 71.6 |
| 7 | Continuous | 1.200 | 1.48 | CH₂Cl₂ | 20:80 | 30 | 30 min | 86 |
| 8 | Continuous | 1.000 | 1.48 | CH₂Cl₂ | 20:80 | 30 | 30 min | 79 |

[1]Comparative Example.
[2] Test discontinued after approximately 10 minutes, owing to equipment clogging, in particular due to clogging of connection pipe between reactors R1 and R2.

We claim:

1. A process for continuously producing an arylimidoperalkanoic acid having the following formula:

in which n is an integer ranging from 3 to 7; the benzene or naphthalene rings are either unsubstituted, or substituted by one or more carboxy groups; and $R_1$ and $R_2$, which are the same, or different from each other, are selected from the group consisting of H and $C_1$–$C_5$ alkyl groups bearing carboxy, percarboxy, hydroxy (OH), nitro (NO₂) and $C_1$–$C_5$ alkoxy substituents, said process comprising the following steps:

(a) Preparing a solution of an arylimidoalkanoic acid having the following formula:

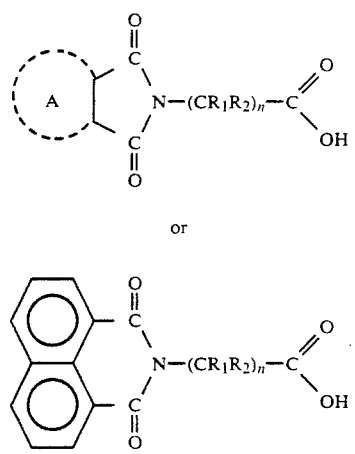

or wherein A, n, $R_1$ and $R_2$ are the same as above, and wherein the benzene or napthalene rings are either unsubstituted, or substituted by one or more carboxy groups, in a halogenated solvent selected from the group consisting of methylene chloride ($CH_2Cl_2$) and trichloromethane ($CHCl_3$), said solution being prepared by dissolving an amount of said arylimidoalkanoic acid which is:
  (i) equal to, or less than the solubility threshold of said arylimidoalkanoic acid in said halogenated solvent at the reaction temperature as defined in step (b) below, and
  (ii) greater than the amount of said arylimidoalkanoic acid which stoichiometrically corresponds to the solubility threshold of said arylimidoperalkanoic acid in said halogenated solvent at the reaction temperature as defined in step (b) below:
(b) continuously reacting the solution prepared in step (a) at a reaction temperature of 10°-35° C., with aqueous $H_2O_2$, in the presence of a string acid selected from the group consisting of $H_2SO_4$, oleum, methanesulfonic acid, trifluoromethanesulfonic acid, fluorosulfonic acid, and mixtures thereof, said strong acid having a molar feed ratio to said arylimidoalkanoic acid of less than 2, to form a reaction product having an aqueous phase and an organic phase;
(c) separating the aqueous phase and the organic phase;
(d) recovering the arylimidoperalkanoic acid from the organic phase; and
(e) recovering the halogenated solvent from the organic phase and recycling said recovered halogenated solvent for use in step (a).

2. The process of claim 1 wherein the Pka value of the strong acid is less than, or equal to 1, and the molar feed ratio of the strong acid to the arylimidoalkanoic acid is less than 1.3.

3. Process according to claim 1 in which said arylimidoperalkanoic acid is selected from among phthalimidoperalkanoic acids of formula (III) and 1,8-naphthaleneimidoperalkanoic acids of formula (IV):

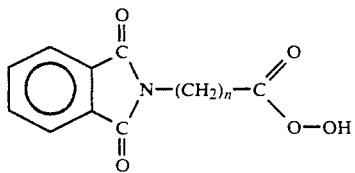

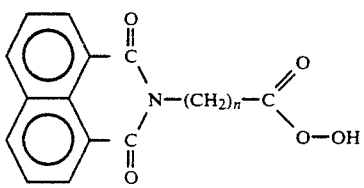

4. The process of claim 3, in which said arylimidoperalilanoic acid is ε-phthalimidoperhexanoic acid (n=5).

5. The process of claim 4, wherein the reaction step (b) occurs inside one or two reactors, said reactor(s) being selected from the group consisting of static mixers, external-recycle reactors and continuous stirred tank reactors, and wherein the solution prepared in step (a), the aqueous $H_2O_2$, and the strong acid are each individually or in combination fed into the reactors at one or more successive feed points.

6. The process of claim 4, wherein the solution prepared in step (a) contains at least 20% by weight of ε-phthalimidohexanoic acid, the aqueous hydrogen peroxide contains 50-90% by weight of $H_2O_2$, and the molar feed ratio of $H_2O_2$ to ε-phthalimidohexanoic acid is in the range of 1.01 to 2.

7. The process of claim 4, in which the molar ratio of said strong acid to the arylimidoalkanoic acid to be peroxidized is in the range of from 0.50 to 1.29.

8. The process of claim 6, wherein the solution of step (a) contains 25-30% by weight of ε-phthalimidohexanoic acid, the aqueous hydrogen peroxide contains 60-80% by weight of, and the molar feed ratio of $H_2O_2$ to ε-phthalimidohexanoic acid is in the range of 1.01 to 1.6.

9. The process of claim 7, wherein the solution prepared in step (a) is brought into contact with a solid acid either prior to, or during contact with said strong acid, said solid acid being selected from the group consisting of the cation exchange resins of strong type and zeolite aluminosilicates of PENTASIL type in their acidic form.

10. The process of claim 9, wherein the solid acid is selected from the group consisting of HZSM5 and HZSM11.

11. The process of claim 4, wherein said organic phase is neutralized after being separated to remove residual acidity of said organic phase.

12. The process of claim 11, wherein the neutralization of the organic phase is carried out by using a process selected from the group consisting of:
  (a) washing the organic phase with an alkaline solution, and
  (b) passing the organic phase through a solid neutralizing bed.

13. The process of claim 11, in which deionized water is added to said aqueous phase and/or to the reaction product before the separation, with the amount of deionized water being of from 0.5 to 1.5 liter per each liter of aqueous phase.

14. The process of claim 11, in which the solvent is recovered from the organic phase by cooling, followed by filtration or centrifugation or both.

15. The process of claim 11, in which the solvent is recovered from the organic phase by distillation, with said distillation being selected from among vacuum distillation and steam distillation.

16. The process of claim 11, in which any ε-phthalimidoperhexanoic acid not dissolved in the organic phase is recovered from the aqueous phase by back-extraction with the halogenated reaction solvent.

17. The process of claim 12, wherein the alkaline solution is selected from the group consisting of solutions of $NaHCO_3$, $NaOH$, $Mg(HCO_3)_2$, and mixtures thereof, and the solid neutralizing bed is selected from the group consisting of $NaHCO_3$, $Na_2CO_3$, $MgCO_3$ and mixture thereof.

18. The process of claim 11, in which the organic phase is neutralized by adding an alkali-earth salt thereto.

19. The process of claim 18, wherein the alkali-earth salt is magnesium sulfate.

* * * * *